(12) United States Patent
Oh et al.

(10) Patent No.: US 12,121,710 B2
(45) Date of Patent: Oct. 22, 2024

(54) DEVICE FOR CUTTING, SEPARATION, AND DISCHARGE OF SYRINGE

(71) Applicant: MUNE, Seoul (KR)

(72) Inventors: Kwang-Bin Oh, Seoul (KR); You-Hwa Kim, Chungcheongnam-do (KR); Jae-Hak Jeong, Goyang-si (KR); Nam-Young Kim, Busan (KR); Ju-Hwan Noh, Seoul (KR); Ji-Won Yun, Seoul (KR)

(73) Assignee: MUNE, Seoul (KR)

( * ) Notice: Subject to any disclaimer, the term of this patent is extended or adjusted under 35 U.S.C. 154(b) by 711 days.

(21) Appl. No.: 17/419,551

(22) PCT Filed: Dec. 16, 2019

(86) PCT No.: PCT/KR2019/017799
§ 371 (c)(1),
(2) Date: Jun. 29, 2021

(87) PCT Pub. No.: WO2020/141759
PCT Pub. Date: Jul. 9, 2020

(65) Prior Publication Data
US 2022/0072240 A1    Mar. 10, 2022

(30) Foreign Application Priority Data

Dec. 31, 2018 (KR) .......... 10-2018-0173609

(51) Int. Cl.
*A61M 5/32* (2006.01)

(52) U.S. Cl.
CPC ........ *A61M 5/3276* (2013.01); *A61M 5/3278* (2013.01); *A61M 2005/3206* (2013.01); *A61M 2005/3282* (2013.01)

(58) Field of Classification Search
CPC .............. A61M 5/3276; A61M 5/3278; A61M 2005/3279; A61M 2005/3206;
(Continued)

(56) References Cited

U.S. PATENT DOCUMENTS

| 5,351,381 A * | 10/1994 | Case ................... A61M 5/3278 29/722 |
| 2004/0186426 A1* | 9/2004 | Allard .............. A61B 5/150732 604/110 |

(Continued)

FOREIGN PATENT DOCUMENTS

| EP | 2420279 A2 | 2/2012 |
| KR | 10-1994-7001710 A | 6/1994 |

(Continued)

OTHER PUBLICATIONS

International Search Report issued Apr. 6, 2020, corresponding to International Application No. PCT/KR2019/017799.

*Primary Examiner* — Ghassem Alie
(74) *Attorney, Agent, or Firm* — Hauptman Ham, LLP

(57) ABSTRACT

A device for cutting, separation, and discharge of a syringe according to an embodiment of the present disclosure includes a barrel unit, a main body including a driving unit configured to rotate the barrel unit, and a cutting body configured to cut a needle portion of a syringe during rotation of the barrel unit, wherein transfer of the syringe inserted into the barrel unit, cutting of the needle portion, discharge of the needle portion, and discharge of a syringe main body are performed by only one rotation of the barrel unit.

13 Claims, 14 Drawing Sheets

(58) Field of Classification Search
CPC .. A61M 2005/5006; A61M 2005/3282; A61M 5/50; A61M 5/3205; A61M 2205/8206; A61M 2205/33; A61M 2205/273; B26D 7/0641; B26D 2007/0018
USPC .......................................................... 83/944
See application file for complete search history.

(56) References Cited

U.S. PATENT DOCUMENTS

2005/0269226 A1   12/2005  Erickson et al.
2017/0173272 A1*  6/2017  Radmand ............ A61M 5/3276

FOREIGN PATENT DOCUMENTS

| | | |
|---|---|---|
| KR | 10-1995-0002795 A | 2/1995 |
| KR | 10-2000-0028006 A | 5/2000 |
| KR | 10-2002-0036160 A | 5/2002 |
| KR | 20-0472067 Y1 | 4/2014 |
| KR | 10-1619207 B1 | 5/2016 |
| KR | 10-2018-0054320 A | 5/2018 |
| KR | 10-1893573 B1 | 8/2018 |
| KR | 10-1893575 B1 | 8/2018 |
| KR | 10-1893574 B1 | 10/2018 |
| KR | 10-2019-0117088 A | 10/2019 |
| KR | 10-2019-0135113 A | 12/2019 |

\* cited by examiner

DEVICE FOR CUTTING, SEPARATION, AND DISCHARGE OF SYRINGE

CROSS-REFERENCE TO RELATED PATENT APPLICATIONS

This application is a U.S. National Stage Application under 35 U.S.C. § 371 of PCT Application No. PCT/KR2019/017799, filed Dec. 16, 2019, which claims priority to Korean Patent Application No. 10-2018-0173609, filed Dec. 31, 2018, whose entire disclosures are hereby incorporated by reference.

TECHNICAL FIELD

The present disclosure relates to a device for cutting, separation, and discharge of a syringe.

BACKGROUND ART

A syringe is one medical tool and is used for the purpose of injecting drug into the body, collecting blood, or the like. However, used syringes may cause infection of various notifiable communicable diseases and infectious diseases and thus must be safely disposed of.

As a specific example, syringes used as therapeutic tools in medical institutions such as hospitals are prohibited from being reused so as to prevent secondary infection.

In this way, syringes used in hospitals and the like are essentially subjected to a disposal process, but rather than being discarded as it is in the disposal process, the syringe is discarded after the needle and body of the syringe are separated.

In the separation process, there are risks in terms of safety, such as the possibility of accidental cuts.

For example, in order to prevent secondary infection due to discarded syringes, hospitals in some countries use a device for immediate disposal of syringes, such as a device that melts and oxidizes a used syringe with high-temperature heat. However, domestic hospitals still use a conventional method of handling infectious waste (e.g., batch disposal of syringes after collecting the syringes). In the conventional method of handling infectious waste, since a needle is directly removed by hand or by using a protrusion located on a lid of a sharps waste container, there is a problem in that secondary infection may occur in the process due to splashing of blood or a contaminated drug.

In order to prevent such a problem, there is a need for development of technology that allows safe removal of a needle portion of a syringe that is to be discarded after use.

As a related art, Korean Patent Publication No. 10-1995-0002795 discloses technology relating to a syringe needle handling device.

DISCLOSURE

Technical Problem

The present disclosure is directed to providing a device for cutting, separation, and discharge of a syringe that is capable of promptly processing transfer, cutting, and discharge of a syringe in a single cycle using a motor direct-coupling type driving method.

The present disclosure is also directed to providing a device for cutting, separation, and discharge of a syringe that has a simple structure and high product reliability.

The present disclosure is also directed to providing a device for cutting, separation, and discharge of a syringe in which any portion that comes in contact with a syringe is able to be replaced or washed.

The objectives of the present disclosure are not limited to those mentioned above, and other unmentioned objectives and advantages of the present disclosure should be understood from the description below and should be more clearly understood by the embodiments of the present disclosure. Also, it should be apparent that the objectives and advantages of the present disclosure may be realized by means indicated in the claims and combinations thereof.

Technical Solution

One embodiment of the present disclosure provides a device for cutting, separation, and discharge of a syringe, the device including a barrel unit into which a syringe is insertable and which has a needle portion through-hole provided to allow only a needle portion to be cut to pass through a lower end thereof, a main body including an upper shell which has a first groove, a lower shell which has a second groove corresponding to the first groove and is coupled to the upper shell, and a driving unit which is provided between the upper shell and the lower shell and is directly coupled to the barrel unit, which is installed through the first and second grooves, to rotate the barrel unit at a predetermined angle, and a cutting body which is detachable from a lower portion of the main body and includes a cutting blade to cut the needle portion during rotation of the barrel unit, wherein transfer of the inserted syringe, cutting of the needle portion, discharge of the cut needle portion, and discharge of a syringe main body from which the needle portion is removed are performed by only one rotation of the barrel unit.

Also, the barrel unit may include a barrel housing which is vertically installed through the first and second grooves and has an open upper end portion, a lower end portion in which the needle portion through-hole is provided, and both sides connected to the main body, wherein one side is directly coupled to the driving unit to rotate at a predetermined angle, a barrel cover which is coupled to the open upper portion of the barrel housing and has a circular opening to allow insertion of the syringe, and an inner wall member which is stored in a hollow portion of the barrel housing, fixed by coupling of the barrel cover, and configured to accommodate the inserted syringe in an insertion space therein.

Also, the barrel housing may include a first cylindrical body into which the inner wall member is insertable, a first connection member which is connected to the main body from one side of the first cylindrical body along the center of rotation of the barrel unit and connected to an output shaft of the driving unit, and a second connection member which is connected to the main body from the other side of the first cylindrical body toward a direction opposite to the first connection member along the center of rotation of the barrel unit.

Also, the inner wall member may include a second cylindrical body which is inserted into the first cylindrical body and, when the barrel cover is decoupled, able to be withdrawn from the first cylindrical body to the outside and be replaced or washed, an outer diameter expansion portion which is provided at an upper end of the second cylindrical body and formed to protrude in a circumferential direction to have an outer diameter that is greater than that of the second cylindrical body, and a lower end hole which is disposed at the center of a lower end of the second cylindrical body and communicates with the needle portion through-hole.

Also, the barrel cover may include an annular body screw-coupled to the first cylindrical body and an inner diameter shrinkage portion which is provided at an upper end of the annular body, has an inner diameter that is less than that of the annular body, and is configured to fix the outer diameter expansion portion between the first cylindrical body and the inner diameter shrinkage portion, wherein a male screw portion may be formed on an outer circumferential surface of an upper portion of the first cylindrical body, and a female screw portion may be formed on an inner circumferential surface of the annular body.

Also, a battery cover which is openable and closable may be provided at one side of the main body, and when the battery cover is open, a battery cartridge on which a battery is mounted may become detachable.

Also, the driving unit may include a driving motor embedded between the upper shell and the lower shell so as to be disposed at the opposite side of a position where the battery cartridge is mounted while the first and second grooves are disposed therebetween, a motor fixing portion configured to surround and fix the driving motor, and a direct coupling portion configured to directly couple an output shaft of the driving motor and the first connection member to each other in a straight line.

Also, the cutting body may include a detachable body which is detached by sliding through a detachment groove provided in a lower portion of the main body, a curved groove which is provided in an upper portion of the detachable body and formed to be curved and concave along a direction of rotation of the barrel unit while facing a lower end of the barrel unit, an arc-shaped slot which is provided along the direction of rotation of the barrel unit through the curved groove and formed to allow the needle portion of the syringe inserted into the barrel unit to pass therethrough, and a cutting blade which is provided at a tip of the arc-shaped slot to cut the needle portion which rotates in conjunction with the rotation of the barrel unit in a state of passing through the arc-shaped slot.

Also, the cutting blade may be disposed in a shape that blocks the rotating needle portion at the tip of the arc-shaped slot and may be formed to be tilted at a predetermined angle. For example, the cutting blade may be obliquely disposed to form an obtuse angle in a longitudinal direction of the arc-shaped slot, and further, an upward protrusion that protrudes to a predetermined height may be further provided on an upper portion of the cutting body to install the cutting blade to have a vertical slope such that one end portion of the cutting blade is disposed higher than the other end portion thereof. In this way, a contact length between the cutting blade and the needle portion to be cut may be increased, and thus a cutting force may be improved.

Also, the cutting body may include a discharge opening configured to allow the needle portion, which is cut by the cutting blade, to be discharged downward due to its own weight.

Also, the cutting body may include a curved partition which protrudes upward to a predetermined length behind the cutting blade and has a round curved surface formed at one side surface to correspond to the shape of the lower portion of the barrel unit so as not to interfere with the rotation of the barrel unit. Due to the curved partition, the remaining syringe main body from which the needle portion is removed may be safely separated more hygienically in a direction different from a direction in which the needle portion is discharged. For example, the curved partition may prevent a micro-material in the needle portion from splashing on the surroundings when the needle portion is cut and may prevent contamination of the main body.

Also, the cutting body may further include an extending portion formed to extend in the shape of a plate from an upper portion of the curved partition to a height that corresponds to the center of rotation of the barrel unit. The extending portion is a portion protruding past the curved partition and, preferably, may extend to the height corresponding to the center of rotation of the barrel unit. In this way, spillage of a residual material from inside the syringe main body, from which the needle portion is cut, to the outside through the cut portion may be prevented, and a function of preventing contamination of the main body may be further enhanced.

Also, the cutting body may include at least one pair of coupling guides formed at a lower portion thereof, and the coupling guide may cause the cutting body to slide and be coupled to a sharps waste container.

Also, an operation of the driving unit may be controlled by manipulation of a press switch provided on the upper portion of the cutting body or may be controlled by an infrared sensor configured to detect the syringe inserted into the barrel unit.

Also, an angle of rotation at which the driving unit rotates the barrel unit may be within a range that exceeds 90° and is less than 180°, and when the barrel unit rotates at the maximum angle of rotation, the syringe main body remaining in the barrel unit may be separated and discharged in a second direction which is different from a first direction in which the needle portion is discharged.

Advantageous Effects

According to the present disclosure, there is an advantage in that transfer, cutting, and discharge of a syringe can be promptly processed in a single cycle using a motor direct-coupling type driving method. As a result, a syringe handling speed is increased, and thus effects of shortening the work time and reducing costs can be expected.

Also, according to the present disclosure, there is an advantage in that the product reliability can be secured due to a simplified structure and a reduced number of components. Also, due to the motor direct-coupling method, loss due to power transfer can be prevented, and interference between components can be suppressed.

In addition, according to the present disclosure, there is an advantage in that any portion that comes in contact with a syringe can be replaced or washed. For example, an inner wall member of a barrel unit into which a syringe is inserted is a portion that comes in direct contact with the syringe and is replaceable, and detachment of the inner wall member to the outside is prevented by a separate cap such that the position of the inner wall member is fixed. Also, a cutting body at a lower end that includes a cutting blade can be removed and replaced together with the cutting blade corresponding to a replacement cycle of the cutting blade. In this way, according to the present disclosure, the entire process in which a syringe is cut, separated, and discharged is hygienically performed, and components that come in contact with the syringe can be periodically replaced for use.

Specific advantageous effects of the present disclosure in addition to the above-described advantageous effects will be described below while describing details for practicing the disclosure.

MODES OF THE INVENTION

Figure 1:
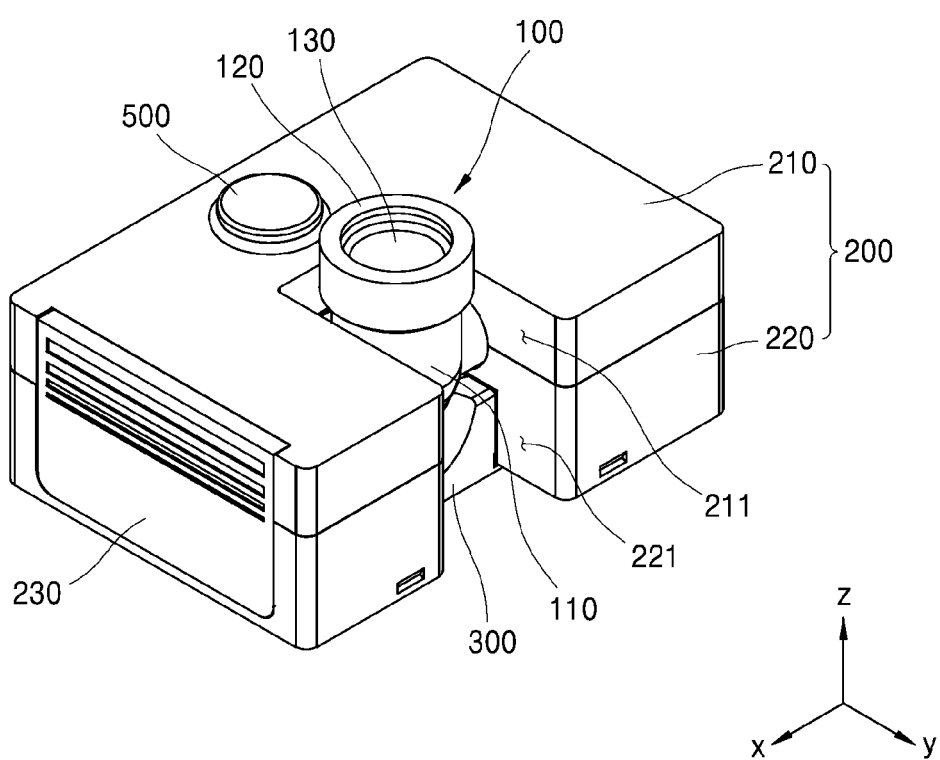
FIG. 1 is a perspective view schematically illustrating a device for cutting, separation, and discharge of a syringe according to an embodiment of the present disclosure.

Hereinafter, embodiments of the present disclosure will be described in detail with reference to the accompanying drawings to allow those of ordinary skill in the art to which the present disclosure pertains to easily practice the present disclosure. The present disclosure may be implemented in various different forms and is not limited to the embodiments described herein.

In order to clearly describe the present disclosure, parts unrelated to the description have been omitted from the drawings, and the same or similar elements will be denoted by the same reference numerals throughout the specification. Also, some embodiments of the present disclosure will be described in detail with reference to the exemplary drawings. In assigning reference numerals to the elements in each drawing, the same reference numerals are assigned to the same elements as much as possible even when the elements are illustrated in different drawings. Also, in describing the present disclosure, when detailed description of a known related configuration or function is deemed to unnecessarily obscure the gist of the present disclosure, the detailed description thereof will be omitted.

In describing the elements of the present disclosure, terms such as first, second, A, B, (a), and (b) may be used. The terms are only for distinguishing the elements from other elements, and the essence, order, sequence, number, or the like of the corresponding elements are not limited by the terms. When a certain element is described as being "connected," "coupled," or "linked" to another element, this may mean that the element is directly connected or linked to the other element but may also be understood that another element is "interposed" between the two elements or the two elements are "connected," "coupled," or "linked" to each other through another element.

Also, in implementing the present disclosure, elements may be subdivided and described for convenience of description, but the elements may be implemented as a single device or module, or one element may be implemented by being divided into a plurality of devices or modules.

Figure 2:
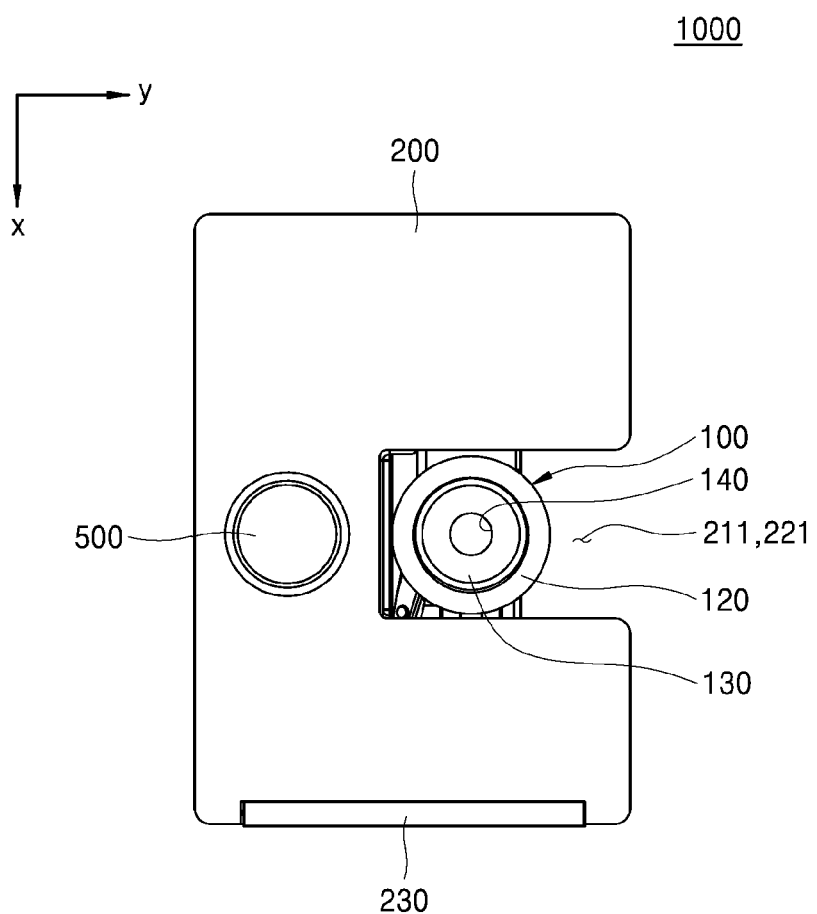
FIG. 2 is a plan view schematically illustrating the device for cutting, separation, and discharge of a syringe according to an embodiment of the present disclosure.
Figure 3:
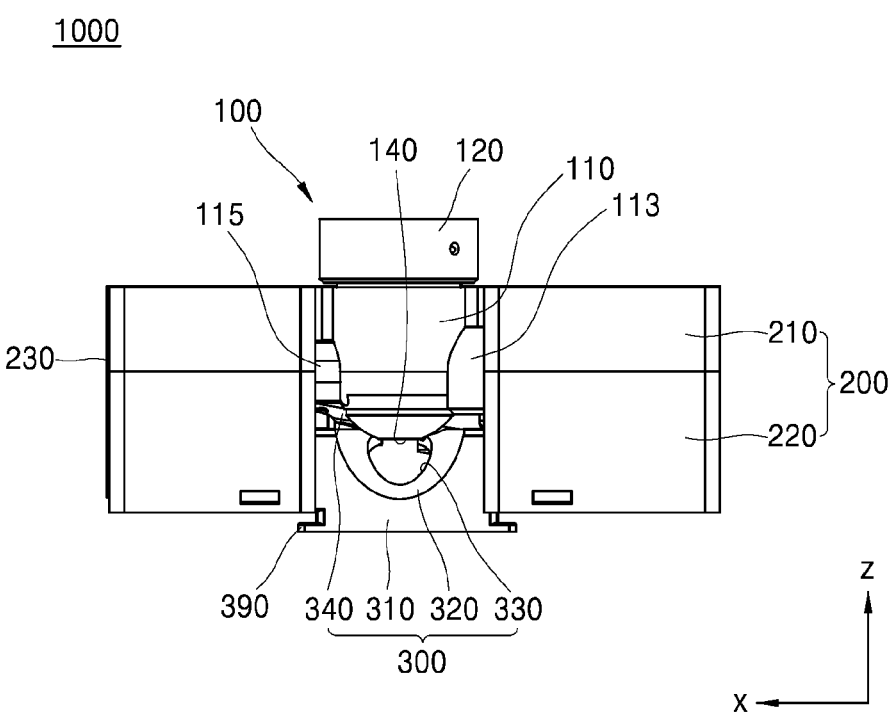
FIG. 3 is a front view schematically illustrating the device for cutting, separation, and discharge of a syringe according to an embodiment of the present disclosure.
Figure 4:
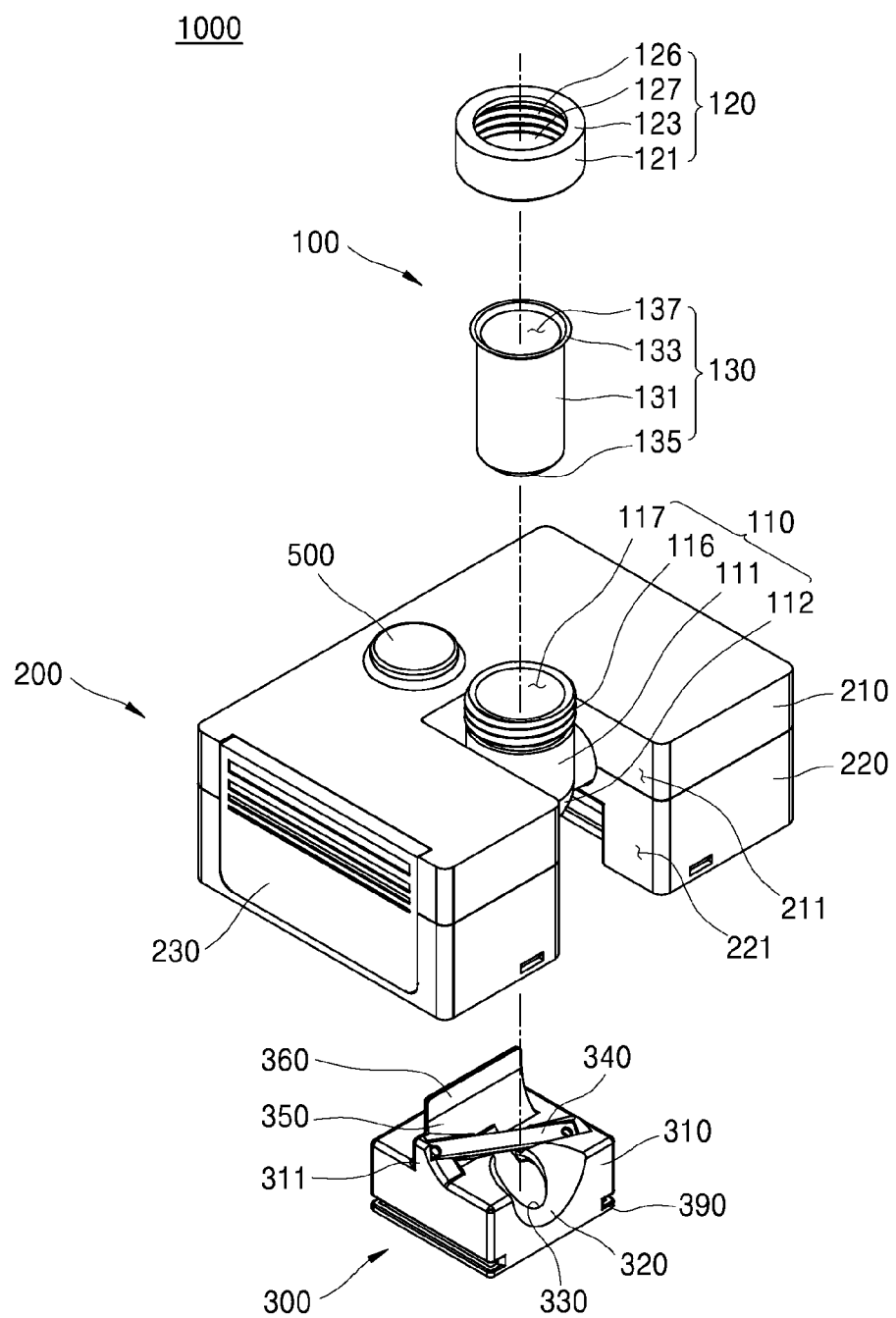
FIGS. 4 and 5 are exploded perspective views schematically illustrating the device for cutting, separation, and discharge of a syringe according to an embodiment of the present disclosure.
Figure 5:
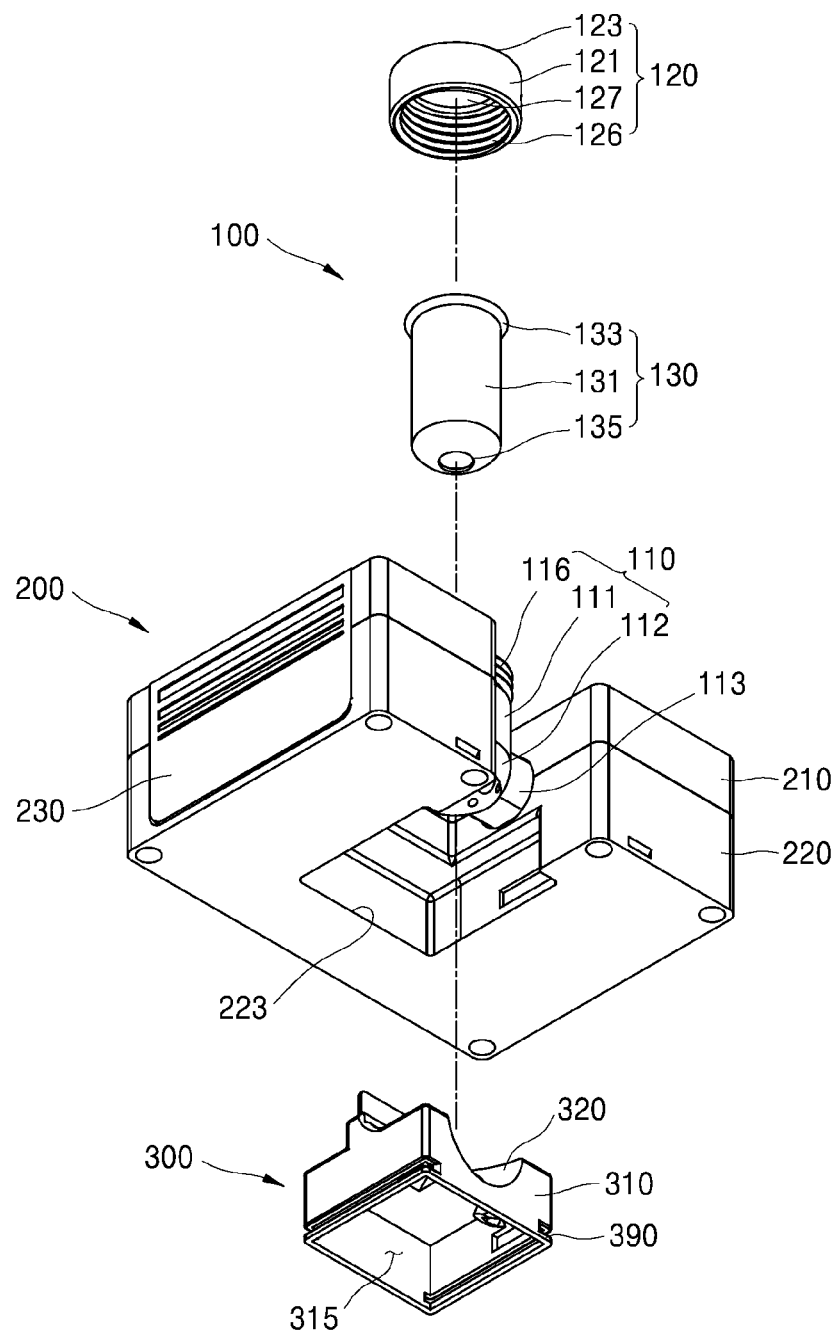

FIGS. 1 to 3 are a perspective view, a plan view, and a front view, respectively, that schematically illustrate a device for cutting, separation, and discharge of a syringe according to an embodiment of the present disclosure, and FIGS. 4 and 5 are exploded perspective views schematically illustrating the device for cutting, separation, and discharge of a syringe according to an embodiment of the present disclosure.

As illustrated, a device 1000 for cutting, separation, and discharge of a syringe according to an embodiment of the present disclosure includes a barrel unit 100, a main body 200, and a cutting body 300.

The barrel unit 100 is provided in a form into which a syringe S (see FIG. 11) is insertable. The barrel unit 100 includes a needle portion through-hole 140 to allow only a needle portion S1, which is an object to be cut, of the syringe S (see FIG. 11) excluding a body portion S2 thereof to pass through a lower end of the barrel unit 100.

Specifically, the barrel unit 100 includes a barrel housing 110, a barrel cover 120, and an inner wall member 130.

The barrel housing 110 is vertically installed through a first groove 211 and a second groove 221.

The barrel housing 110 has an upper end portion that is open and a lower end portion 112 (see FIG. 5) in which the needle portion through-hole 140 is provided.

Also, the barrel housing 110 has both sides connected to the main body 200. One of the both sides connected to the main body 200 is directly coupled to an output shaft of a driving unit 270 and receives a rotational force without loss due to power transfer and rotates at a predetermined angle.

For example, the barrel housing 110 includes a first cylindrical body 111 (see FIG. 4), a first connection member 113 (see FIG. 3), and a second connection member 115 (see FIG. 3).

The first cylindrical body 111 is formed to have a size into which the inner wall member 130 is insertable.

The first connection member 113 is connected from one side of the first cylindrical body 111 to the main body 200 along the center of rotation of the barrel unit 100. More specifically, the first connection member 113 is directly coupled to the output shaft of the driving unit 270 and receives a rotational force.

The second connection member 115 is connected to the main body 200 from the other side of the first cylindrical body 111 toward a direction opposite to the first connection member 113 along the center of rotation of the barrel unit 100.

In this way, the first and second connection members 113 and 115 have a form extending in a straight line along the center of rotation of the barrel unit 1000 through both sides of the first cylindrical body 111 and thus may be directly coupled to the driving unit 270 and rotate the barrel housing 110 at a predetermined angle.

The barrel cover 120 is coupled to the open upper portion of the barrel housing 110.

The barrel cover 120 includes a circular opening 127 for insertion of the syringe S.

For example, the barrel cover 120 includes an annular body 121 and an inner diameter shrinkage portion 123.

The annular body 121 is screw-coupled to the first cylindrical body 111.

The inner diameter shrinkage portion 123 is provided at an upper end of the annular body 121 and has an inner diameter that is less than that of the annular body 121. Accordingly, when the barrel cover 120 is coupled to the barrel housing 110, an outer diameter expansion portion 133 may be confined between an upper end of the first cylindrical body 111 and the inner diameter shrinkage portion 123, and thus separation and detachment of the inner wall member 130 may be prevented.

For example, as illustrated in FIGS. 4 and 5, a male screw portion 116 may be formed on an outer circumferential surface of an upper portion of the first cylindrical body 111, and a female screw portion 126 may be formed on an inner circumferential surface of the annular body 121. In this way, fastening and decoupling between the barrel housing 110 and the barrel cover 120 become easy, and thus replacement and washing of the inner wall member 130 may be facilitated.

The inner wall member 130 is stored in a hollow portion 117 of the barrel housing 110 and is confined and fixed when the barrel cover 120 is coupled. Also, the syringe S (see FIG. 11) inserted into the barrel unit 100 is accommodated in an insertion space 137 provided inside the inner wall member 130.

For example, as illustrated in FIGS. 4 and 5, the inner wall member 130 includes a second cylindrical body 131, the outer diameter expansion portion 133, and a lower end hole 135.

The second cylindrical body 131 is inserted into the first cylindrical body 111. The second cylindrical body 131 may be withdrawn from the first cylindrical body 111 to the outside when the barrel cover 120 is decoupled. In this way, when necessary, the second cylindrical body 131 may be replaced with a new one or may be washed for hygienic use.

The outer diameter expansion portion 133 is provided at an upper end of the second cylindrical body 131. Specifically, the outer diameter expansion portion 133 is formed to protrude in a circumferential direction to have an outer diameter that is greater than that of the second cylindrical body 131 and is confined by the inner diameter shrinkage portion 123 of the barrel cover 120, which will be described below, and prevents separation and detachment of the inner wall member 130.

The lower end hole 135 is disposed at the center of a lower end of the second cylindrical body 131 and is formed to communicate with the needle portion through-hole 140. Accordingly, the needle portion S1 (see FIG. 11) of the syringe S (see FIG. 11) inserted into the insertion space 137 of the inner wall member 130 may pass through the lower end hole 135 and then protrude a predetermined length to the outside through the needle portion through-hole 140.

The main body 200 includes an upper shell 210 which has the first groove 211 and a lower shell 220 which has the second groove 221 corresponding to the first groove 211 and is coupled to the upper shell 210, and the upper and lower shells 210 and 220 are vertically coupled to constitute the overall exterior.

Also, the main body 200 includes the driving unit 270. The driving unit 270 is provided between the upper shell 210 and the lower shell 220 and is directly coupled to the barrel unit 100, which is installed through the first and second grooves 211 and 221, to provide a rotational force to the barrel unit 100. Accordingly, the barrel unit 100 may rotate at a predetermined angle in a state in which the syringe S (see FIG. 11) is inserted thereinto.

Meanwhile, a battery cover 230 which is openable and closable is provided at one side of the main body 200.

Figure 6:
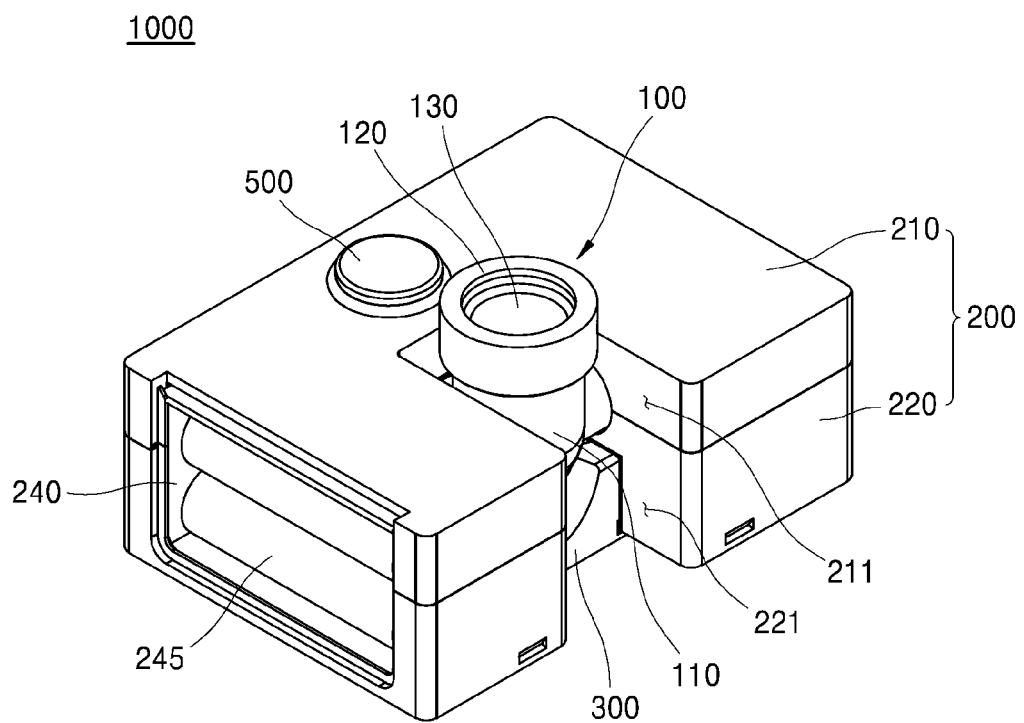
FIG. 6 is a perspective view showing a state in which a battery cover provided to a main body is open in the device for cutting, separation, and discharge of a syringe according to an embodiment of the present disclosure.
Figure 7:
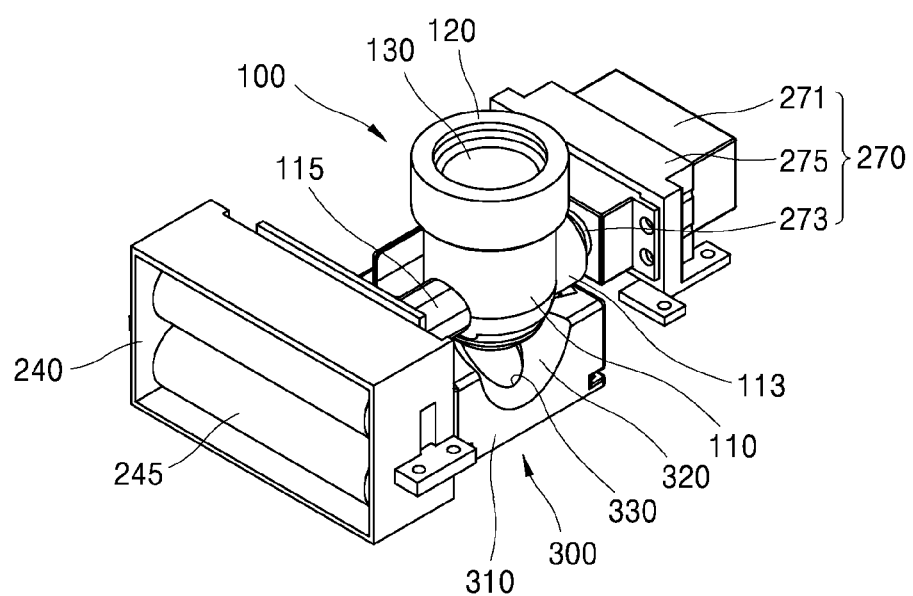
FIG. 7 is a perspective view showing an internal configuration in which an upper shell and a lower shell of FIG. 6 are decoupled.
Figure 8:
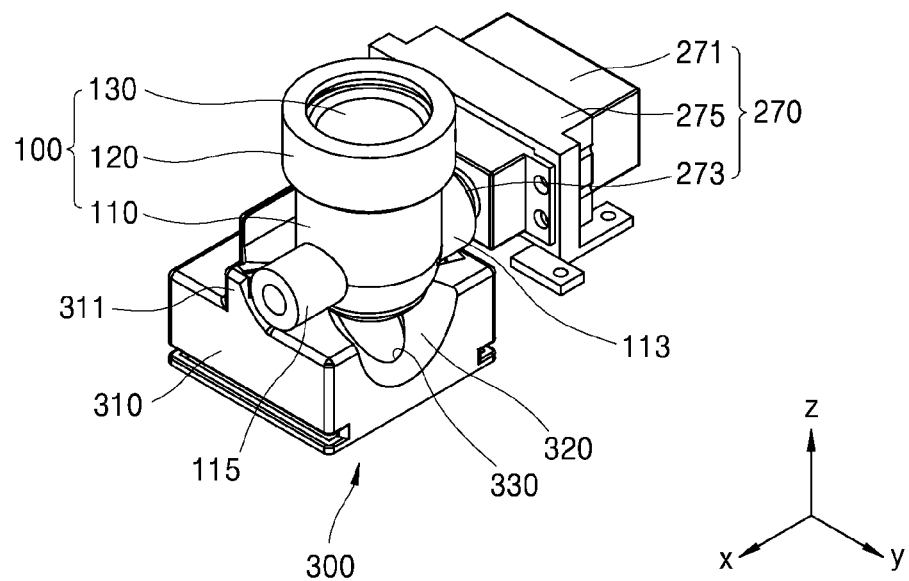
FIG. 8 is a perspective view showing a coupling structure of a barrel unit, a driving unit, and a cutting body in the device for cutting, separation, and discharge of a syringe according to an embodiment of the present disclosure.
Figure 9:
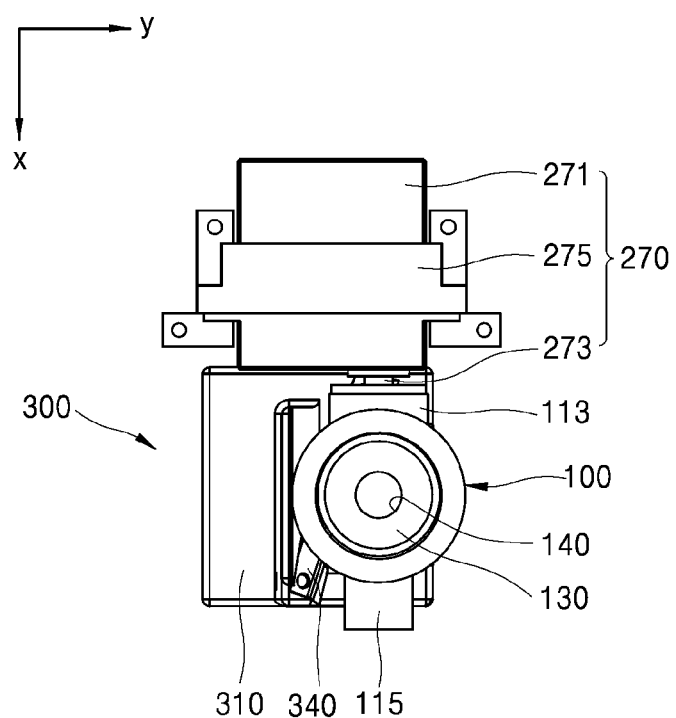
FIG. 9 is a lateral view showing the coupling structure of the barrel unit, the driving unit, and the cutting body in the device for cutting, separation, and discharge of a syringe according to an embodiment of the present disclosure.
Figure 10:
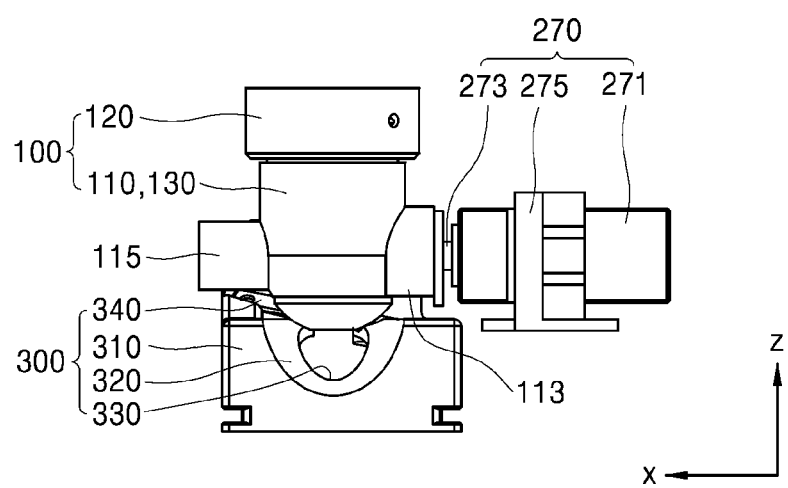
FIG. 10 is a front view showing the coupling structure of the barrel unit, the driving unit, and the cutting body in the device for cutting, separation, and discharge of a syringe according to an embodiment of the present disclosure.

FIG. 6 is a perspective view showing a state in which a battery cover provided to a main body is open in the device for cutting, separation, and discharge of a syringe according to an embodiment of the present disclosure. Referring to FIG. 6, when the battery cover 230 is open, detachment of a battery cartridge 240 in which a battery 245 is mounted becomes possible. The driving unit 270 (see FIG. 7) may receive power by the battery 245. In addition, although not illustrated, the driving unit 270 may be operated by receiving external power using a wired cable or the like.

As illustrated in FIGS. 7 to 10, the driving unit 270 includes a driving motor 271, a motor fixing portion 275, and a direct coupling portion 273.

Referring to FIGS. 7 to 10, the driving motor 271 is embedded between the upper shell 210 (see FIG. 6) and the lower shell 220 (see FIG. 6) so as to be disposed at the opposite side of a position where the battery cartridge 240 is mounted while the first and second grooves 211 and 221 (see FIG. 6) are disposed therebetween.

The motor fixing portion 275 is a support member configured to surround and fix the driving motor 271. According to the drawings, the motor fixing portion 275 is formed in a quadrilateral shape to allow the driving motor 271 to be inserted through a quadrilateral space inside the motor fixing portion 275 and fixed. However, the shape of the motor fixing portion 275 may be changed.

The direct coupling portion 273 is a member configured to directly connect an output shaft of the driving motor 271 and the first connection member 113 in a straight line. An axial connection connector or the like may be used therefor.

In this way, since the output shaft of the single driving motor 271 is directly coupled to the barrel unit 100 and may transmit a rotational force thereto without change, loss due to power transfer may be reduced. Also, there are advantages in that the number of used components is reduced, the structure is simplified, and the product reliability is improved.

The cutting body 300 is detachably coupled to a lower portion of the main body 200. Therefore, when necessary, the cutting body 300 may be replaced or washed. Preferably, the cutting body 300 may be replaced together with a cutting blade 340 corresponding to a replacement cycle of the cutting blade 340.

The cutting body 300 may include the cutting blade 340 configured to cut the needle portion S1 (see FIG. 11), which is an object to be cut, during rotation of the barrel unit 100.

As a specific example, referring to FIGS. 4 and 5, the cutting body 300 includes a detachable body 310, a curved groove 320, an arc-shaped slot 330, and the cutting blade 340.

The detachable body 310 is formed in a shape that is able to slide and be detached through a detachment groove 223 (see FIG. 5) provided in the lower portion of the main body 200.

The curved groove 320 is provided in an upper portion of the detachable body 310. The curved groove 320 is formed to be curved and concave along a direction of rotation of the barrel unit 100 while facing a lower end of the barrel unit 100, more specifically, the lower end portion 112 of the barrel housing 110.

The arc-shaped slot 330 is provided along the direction of rotation of the barrel unit 100 through the curved groove 320. The needle portion S1 (see FIG. 11) of the syringe inserted into the barrel unit 100 passes through the arc-shaped slot 330 and protrudes downward.

Figure 11:
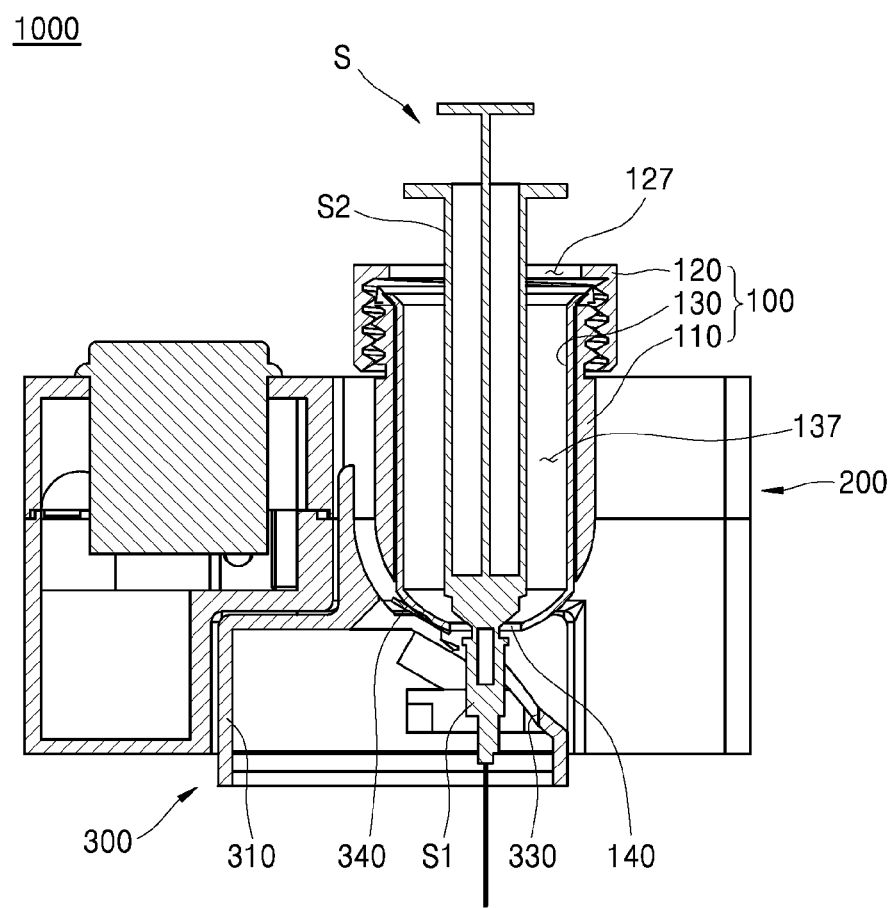
FIGS. 11 to 14 are views for describing an operational relationship of the device for cutting, separation, and discharge of a syringe according to an embodiment of the present disclosure.

The cutting blade 340 is provided at a tip of the arc-shaped slot 330 to cut the needle portion S1 (see FIG. 11). In other words, the cutting blade 340 cuts the needle portion S1 (see FIG. 11) which rotates in conjunction with the rotation of the barrel unit 100 in a state of passing through the arc-shaped slot 330.

Meanwhile, the cutting blade 340 is disposed in a shape that blocks the rotating needle portion S1 (see FIG. 11) at the tip of the arc-shaped slot 330. Preferably, the cutting blade 340 may be formed to be tilted at a predetermined angle instead of having a shape that blocks the rotating needle portion S1 (see FIG. 11) in a direction orthogonal (90°) to the arc-shaped slot 330.

In this way, the cutting blade 340 is obliquely disposed to form an obtuse angle with respect to a longitudinal direction of the arc-shaped slot 330. This is to increase a contact length with the cutting blade 340 and improve cutting performance.

In addition, an upward protrusion 311 that protrudes to a predetermined height may be further provided on an upper portion of the detachable body 310 to install the cutting blade 340 to have a vertical slope such that one end portion of the cutting blade 340 is disposed higher than the other end portion thereof. In this way, a contact length between the cutting blade 340 and the needle portion S1 (see FIG. 11), which is an object to be cut, may be increased, and thus a cutting force may be improved.

Meanwhile, referring to FIG. 5, the cutting body 300 may further include a discharge opening 315 through a lower portion of the detachable body 310.

The discharge opening 315 allows the needle portion S1 (see FIG. 11), which is cut by the cutting blade 340, to be discharged downward due to its own weight to allow only the cut needle portion S1 (see FIG. 11) to be automatically inserted into a sharps waste container.

Also, the cutting body 300 may further include a curved partition 350.

The curved partition 350 protrudes upward to a predetermined length behind the cutting blade 340 and has a round curved surface formed at one side surface to correspond to the shape of the lower portion of the barrel unit 100 so as not to interfere with the rotation of the barrel unit 100. Accordingly, due to the curved partition 350, the remaining body portion S2 (see FIG. 11) of the syringe from which the needle portion S1 (see FIG. 11) is removed may be safely separated and discharged hygienically in a direction different from a direction in which the needle portion is discharged. For example, the curved partition 350 may prevent a micro-material in the needle portion S1 (see FIG. 11) from splashing on the surroundings when the needle portion S1 (see FIG. 11) is cut and may prevent contamination of the main body 200.

Also, the cutting body 300 may further include an extending portion 360 which extends from an upper portion of the curved partition 350.

The extending portion 360 is formed to extend in the shape of a plate from the upper portion of the curved partition 350 to a height that corresponds to the center of rotation of the barrel unit 100.

For example, the extending portion 360 is a portion protruding past the curved partition 350 and, preferably, may extend to the height corresponding to the center of rotation of the barrel unit 100. In this way, spillage of a residual material from inside the body portion S2 (see FIG. 11) of the syringe, from which the needle portion S1 (see FIG. 11) is cut, to the outside through the cut portion may be prevented, and a function of preventing contamination of the main body 200 may be further enhanced.

Also, at least one pair of coupling guides 390 (see FIG. 5) may be provided at a lower portion of the cutting body 300. The coupling guide 390 is a portion used when causing the cutting body 300 to slide and be coupled to the sharps waste container. The shape of the coupling guide 390 is not necessarily limited to the illustrated shape and may be changed to another shape.

Meanwhile, an operation of the driving unit 270 illustrated in FIGS. 7 to 10 may be controlled by manipulation of a press switch 500 (see FIG. 1) provided on the upper portion of the main body 200 (see FIG. 1). In addition, an operation of the driving unit 270 may be controlled using an infrared sensor configured to detect the syringe S inserted into the barrel unit 100.

An angle of rotation at which the driving unit 270 rotates the barrel unit 100 is within a range that exceeds 90° and is less than 180°, and when the barrel unit 100 rotates at the maximum angle of rotation (see FIG. 14), the body portion S2 of the syringe that remains in the barrel unit 100 is separated and discharged in a second direction W2 (see FIG. 14) which is different from a first direction W1 (see FIG. 14) in which the needle portion S1 is discharged.

Hereinafter, an operational relationship of the device 1000 for cutting, separation, and discharge of a syringe according to an embodiment of the present disclosure will be described in detail with reference to FIGS. 11 to 14.

FIGS. 11 to 14 are views for describing an operational relationship of the device for cutting, separation, and discharge of a syringe according to an embodiment of the present disclosure.

Referring to FIG. 11, the syringe S is inserted into the barrel unit 100. The body portion S2 of the syringe is accommodated in the insertion space 137 of the inner wall member 130 through the circular opening 127 of the barrel cover 120. Here, the needle portion S1 passes through the needle portion through-hole 140 provided in the lower end of the barrel unit 100 and protrudes downward. The needle portion S1 may pass through the arc-shaped slot 330 and protrude further downward than the lower end of the cutting body 300. Here, the needle portion S1 refers to a portion which includes a syringe needle and is cut from the syringe instead of referring to the syringe needle itself.

Figure 12:
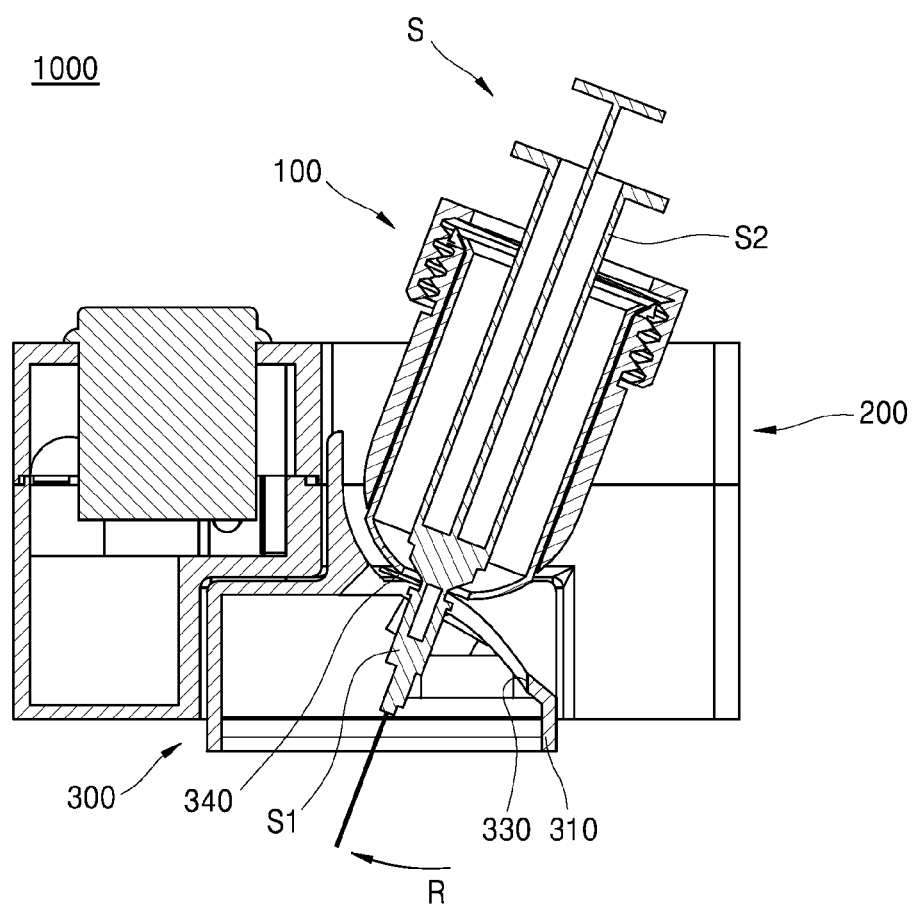

Next, referring to FIG. 12, the barrel unit 100 rotates in a predetermined rotational direction R and transfers the syringe S in the direction R. Here, in a state of passing through the arc-shaped slot 330, the needle portion S1 is cut by the cutting blade 340 while rotating in the direction R.

Figure 13:
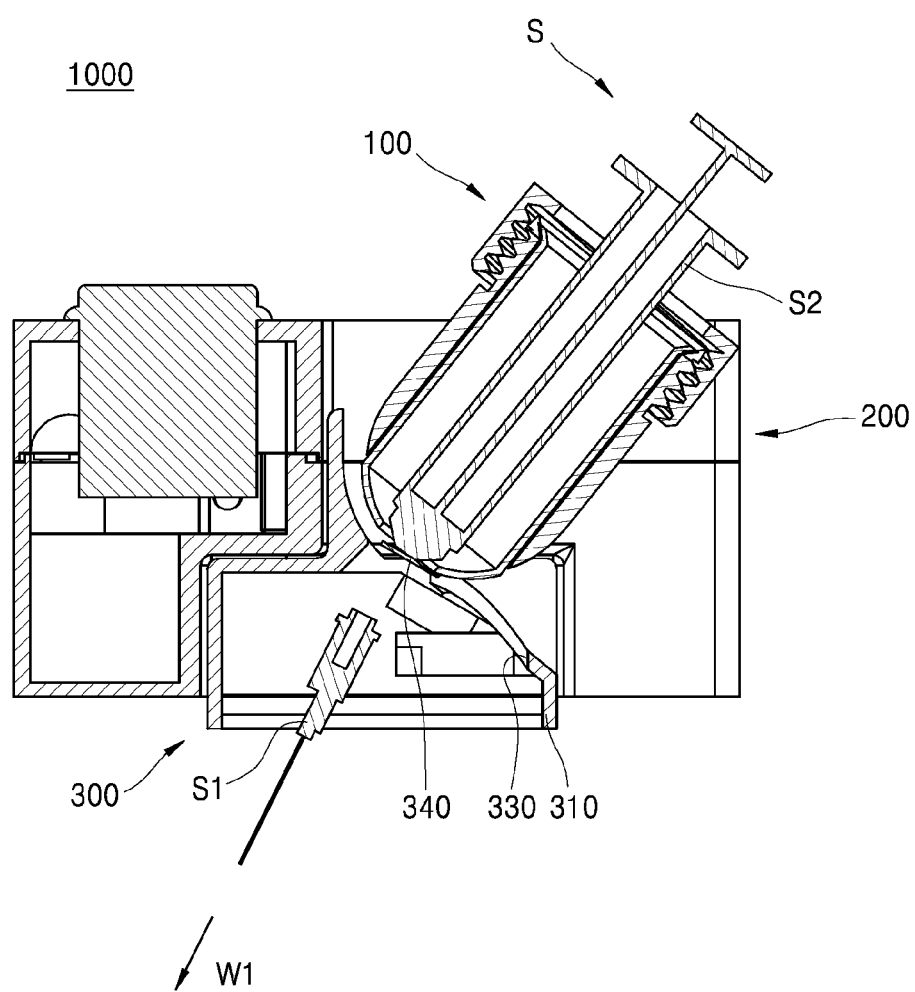

Next, referring to FIG. 13, the cut needle portion S1 is discharged to the lower portion of the cutting body 300 in the first direction W1 due to its own weight and may be separated and discharged to the inside of the sharps waste container.

The device 1000 for cutting, separation, and discharge of a syringe according to an embodiment of the present disclosure implements, in addition to an operation of cutting the needle portion S1 illustrated in FIG. 13, an operation of automatically separating and discharging the body portion S2 of the syringe that remains in the barrel unit 100 after the needle portion S1 is removed.

Figure 14:
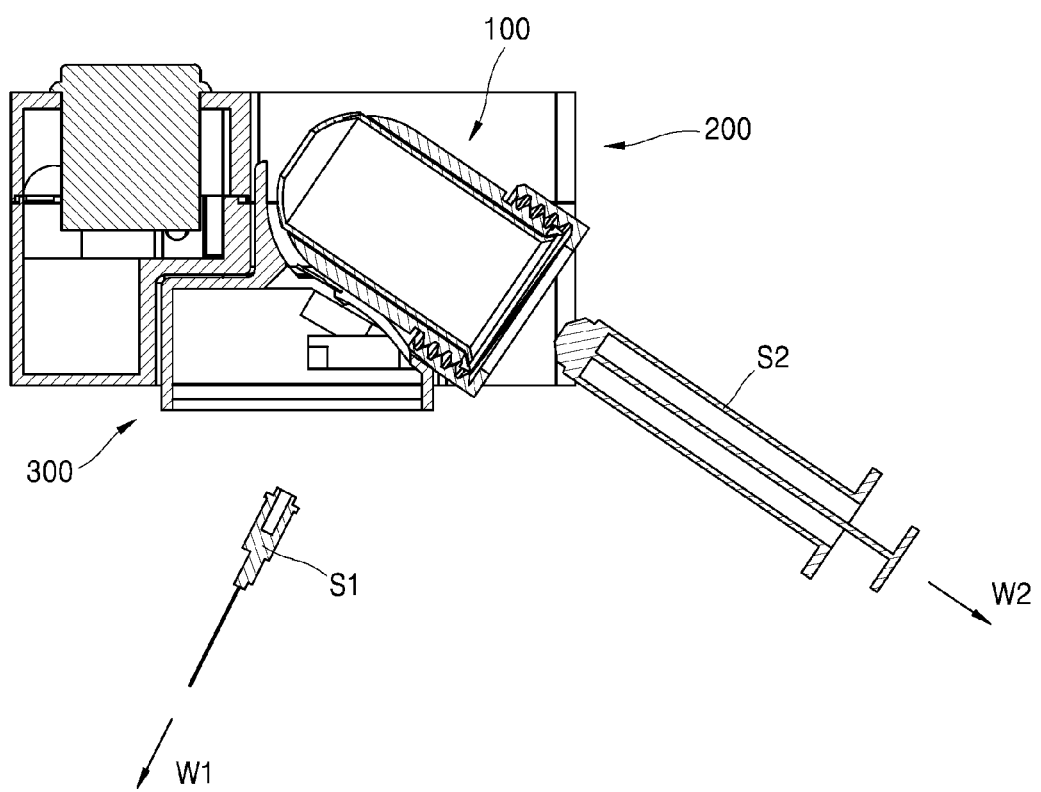

Referring to FIG. 14, even after the needle portion S1 is cut, the barrel unit 100 rotates further in the predetermined rotational direction R (see FIG. 12) within an angle-of-rotation range that exceeds 90° and is less than 180°. In this way, the body portion S2 remaining in the barrel unit 100 may also be separated and discharged in the second direction W2, which is different from the first direction W1 in which the needle portion S1 is discharged, using an automated method.

The device 1000 for cutting, separation, and discharge of a syringe according to an embodiment of the present disclosure configured as described above has an advantage in that, by the barrel unit 100 rotating only one time at an angle of rotation that exceeds 90° and is less than 180°, all of transfer of a syringe, cutting of a needle portion of the syringe, discharge of the cut needle portion, and discharge of a body portion of the syringe that remains after the needle portion is removed are continuously performed.

Further, the device 1000 for cutting, separation, and discharge of a syringe according to an embodiment of the present disclosure may further include an image processing module that is capable of, in addition to detecting whether a syringe is inserted, analyzing the type of the inserted syringe through image analysis. Information acquired during insertion of a syringe into the device 1000 may be compared with prescription and usage history of the syringe to collect data at the time of disposal of the syringe. In this way, the overall life cycle of the syringe may be monitored.

As described above, according to the configuration and action of the present disclosure, there are the following favorable technical effects.

According to the present disclosure, there is an advantage in that transfer, cutting, and discharge of a syringe can be promptly processed in a single cycle using a motor direct-coupling type driving method. As a result, a syringe handling speed is increased, and thus effects of shortening the work time and reducing costs can be expected.

Also, a simplified structure and a reduced number of components contribute to securing the product reliability. Also, due to the motor direct-coupling method, loss due to power transfer may be prevented, and interference between components may be suppressed.

In addition, there is an advantage in that any portion that comes in contact with a syringe may be replaced or washed.

For example, an inner wall member of a barrel unit into which a syringe is inserted is a portion that comes in direct contact with the syringe and is replaceable, and a cutting body at a lower end that includes a cutting blade may be removed and replaced together with the cutting blade corresponding to a replacement cycle of the cutting blade.

In this way, the entire process in which a syringe is cut, separated, and discharged may be hygienically performed, and components that come in contact with the syringe may be periodically replaced for use.

The present disclosure has been described above with reference to the accompanying drawings, but the present disclosure is not limited by the embodiments disclosed herein and the drawings, and it is apparent that various modifications may be made by those of ordinary skill in the art within the scope of the technical spirit of the present disclosure.

The invention claimed is:

1. A device for cutting, separation, and discharge of a syringe, the device comprising:
   a barrel unit into which a syringe is insertable and which has a needle portion through-hole provided to allow only a needle portion to be cut to pass through a lower end thereof;
   a main body including
      an upper shell which has a first groove,
      a lower shell which has a second groove corresponding to the first groove and is coupled to the upper shell, and
      a driving unit which is provided between the upper shell and the lower shell and is directly coupled to the barrel unit, which is installed through the first and second grooves, to rotate the barrel unit at a predetermined angle; and
   a cutting body which is detachable from a lower portion of the main body and includes a cutting blade to cut the needle portion during rotation of the barrel unit,
   wherein
   the barrel unit, the main body, and the cutting body are configured such that transfer of the inserted syringe, cutting of the needle portion, discharge of the cut needle portion, and discharge of a syringe main body from which the needle portion is removed are performed by only one rotation of the barrel unit,
   the cutting body includes:
      a detachable body which is detachable from the lower portion of the main body by sliding through a detachment groove provided in the lower portion of the main body;
      a curved groove which is provided in an upper portion of the detachable body and formed to be curved and concave along a direction of rotation of the barrel unit while facing a lower end of the barrel unit, the curved groove being curved and concave away from the lower end of the barrel unit in a vertical direction;
      an arc-shaped slot which is provided along the direction of rotation of the barrel unit through the curved groove and configured to allow the needle portion of the syringe inserted into the barrel unit to pass therethrough; and
      a cutting blade which is provided at a tip of the arc-shaped slot and configured to cut the needle portion in response to the needle portion rotating in conjunction with the rotation of the barrel unit in a state of passing through the arc-shaped slot.

2. The device of claim 1, wherein the barrel unit includes:
   a barrel housing which is vertically installed through the first and second grooves and has an open upper end portion, a lower end portion in which the needle portion through-hole is provided, and both sides connected to the main body, wherein one side is directly coupled to the driving unit to rotate at a predetermined angle;
   a barrel cover which is coupled to the open upper portion of the barrel housing and has a circular opening to allow insertion of the syringe; and
   an inner wall member which is stored in a hollow portion of the barrel housing, fixed by coupling of the barrel cover, and configured to accommodate the inserted syringe in an insertion space therein.

3. The device of claim 2, wherein the barrel housing includes:
   a first cylindrical body into which the inner wall member is insertable;
   a first connection member which is connected to the main body from one side of the first cylindrical body along the center of rotation of the barrel unit and connected to an output shaft of the driving unit; and a second connection member which is connected to the main body from the other side of the first cylindrical body toward a direction opposite to the first connection member along the center of rotation of the barrel unit.

4. The device of claim 3, wherein the inner wall member includes:
a second cylindrical body which is inserted into the first cylindrical body and, when the barrel cover is decoupled, able to be withdrawn from the first cylindrical body to the outside and be replaced or washed;
an outer diameter expansion portion which is provided at an upper end of the second cylindrical body and formed to protrude in a circumferential direction to have an outer diameter that is greater than that of the second cylindrical body; and
a lower end hole which is disposed at the center of a lower end of the second cylindrical body and communicates with the needle portion through-hole.

5. The device of claim 4, wherein the barrel cover includes:
an annular body screw-coupled to the first cylindrical body; and
an inner diameter shrinkage portion which is provided at an upper end of the annular body, has an inner diameter that is less than that of the annular body, and is configured to fix the outer diameter expansion portion between the first cylindrical body and the inner diameter shrinkage portion.

6. The device of claim 3, wherein a battery cover which is openable and closable is provided at one side of the main body, and when the battery cover is open, a battery cartridge on which a battery is mounted becomes detachable.

7. The device of claim 6, wherein the driving unit includes:
a driving motor embedded between the upper shell and the lower shell so as to be disposed at the opposite side of a position where the battery cartridge is mounted while the first and second grooves are disposed therebetween;
a motor fixing portion configured to surround and fix the driving motor; and
a direct coupling portion configured to directly couple an output shaft of the driving motor and the first connection member to each other in a straight line.

8. The device of claim 1, wherein the cutting body includes a discharge opening configured to allow the needle portion, which is cut by the cutting blade, to be discharged downward due to its own weight.

9. The device of claim 1, wherein at least one pair of coupling guides is provided at a lower portion of the cutting body, and the at least one pair of coupling guides is configured to cause the cutting body to slide and be coupled to a sharps waste container.

10. The device of claim 1, wherein an operation of the driving unit is controlled by manipulation of a press switch provided on the upper portion of the main body.

11. The device of claim 1, wherein:
an angle of rotation at which the driving unit rotates the barrel unit is within a range that exceeds 90° and is less than 180°; and
when the barrel unit rotates at a maximum angle of rotation, the syringe main body remaining in the barrel unit is separated and discharged in a second direction which is different from a first direction in which the needle portion is discharged.

12. The device of claim 1, wherein an operation of the driving unit is controlled by an infrared sensor configured to detect the syringe inserted into the barrel unit.

13. The device of claim 1, wherein the detachable body is detachable from the lower portion of the main body in a horizontal direction by sliding through the detachment groove provided in the lower portion of the main body.

* * * * *